United States Patent [19]

Bertelli

[11] 4,081,541

[45] * Mar. 28, 1978

[54] STEROID DERIVATIVES

[75] Inventor: Aldo Bertelli, Milan, Italy

[73] Assignee: Rorer Italiana S.p.A., Milan, Italy

[*] Notice: The portion of the term of this patent subsequent to Mar. 8, 1994, has been disclaimed.

[21] Appl. No.: 755,015

[22] Filed: Dec. 28, 1976

[51] Int. Cl.² ............................................. A61K 31/56
[52] U.S. Cl. ................................ 424/243; 260/397.45
[58] Field of Search .................................... 260/397.45

[56] References Cited

U.S. PATENT DOCUMENTS 4,011,317  3/1977  Bertelli ........................... 260/397.45

Primary Examiner—Elbert L. Roberts
Attorney, Agent, or Firm—Young & Thompson

[57] ABSTRACT

The present invention is concerned with new derivatives of the cortisone series having in particular a corticoidal, anti-phlogistic and anti-anaphylactic activity.

The compounds of the present invention are represented by the formula:

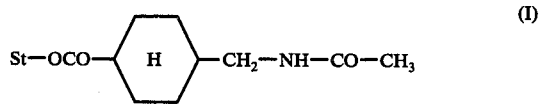

(I)

in which:

St is a radical selected from 9-chloro-11β,17,21-trhihydroxy-16β-methyl-pregna-1,4 diene-3,20 dione and 9-fluoro-11β,17,21 -trihydroxy-16-α-methyl-pregna-1,4 diene-3,20 dione, the ester linkage being at position 21 of the steroid group.

5 Claims, No Drawings

STEROID DERIVATIVES

The present invention is concerned with new derivatives of the cortisone series having in particular a corticoidal, anti-phlogistic and anti-anaphylactic activity and their therapeutic preparations.

The compounds of the present invention are represented by the formula:

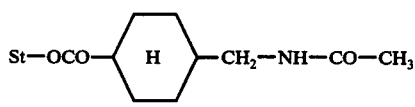
(I)

in which:

St represents a radical selected from 9-chloro-11β,17,21-trihydroxy-16β-methyl-pregna-1,4 diene-3,20-dione; 9-fluoro-11β,17,21-trihydroxy-16α-methyl-pregna-1,4 diene-3,20-dione.

The invention also provides a process for the preparation of compounds of formula (I) in which the steroid is reacted with the acid chloride of 4-N-acetylaminomethylcyclohexanecarboxylic acid in a suitable organic solvent (for example chloroform or benzene), in the presence of a hydrochloric acid acceptor (for example pyridine).

The following non-limitative examples illustrate the preparation of the compounds according to the invention.

EXAMPLE 1

Preparation of beclomethasone 21-(4-N-acetylaminomethylcyclohexane carboxylate).

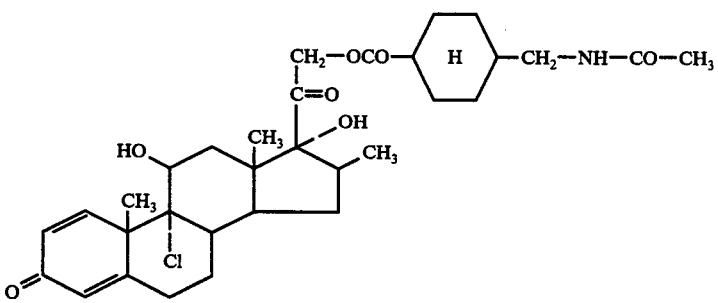

a. Preparation of 4-N-acetylaminomethylcyclohexanecarboxylic acid:

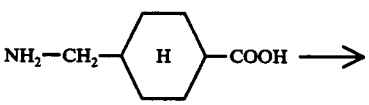
(II)

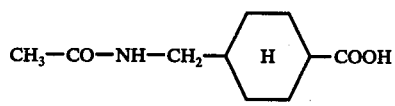

20 grams of aminomethylcyclohexanecarboxylic acid dissolved in 100 cm³ of anhydrous pyridine were cooled to 0° to 5° C. 15 cm³ of acetic anhydride were added to this solution with stirring without exceeding 10° C. When the addition was finished, the mixture was allowed to stand for 12 hours, then the solvent was evaporated off under vacuum and the residue was washed up with water. The residue was filtered, then crystallized in water. Melting point 130° C.

b. Preparation of the acid chloride of 4-N-acetylaminomethylcyclohexanecarboxylic acid:

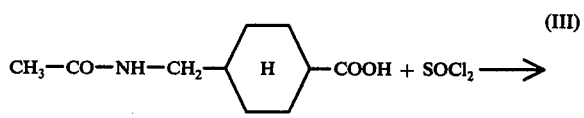
(III)

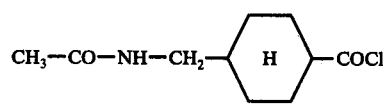

2 grams of the acid (II) were suspended in 10 cm³ of anhydrous benzene and treated, under agitation, with 2 grams of thionyl chloride. After 60 minutes, the solution was diluted with petroleum ether to complete precipitation and then filtered rapidly. 2 grams of the acid chloride were obtained.

c. Preparation of beclomethasone ester:

1 gram of beclomethasone was dissolved in 10 cm³ of a solution obtained by dissolving 0.8 grams of the acid chloride (III) in anhydrous chloroform free of ethanol. The mixture was allowed to stand for 48 hours, and the solvent was evaporated off under vacuum. An oil was obtained which became solid on treatment with a saturated bicarbonate solution. The desired ester was obtained by crystallization from ethanol.

Melting point 222° C; Molecular weight 589.93; Empirical formula $C_{32}H_{44}ClNO_7$; C = 65.09%; H = 7.46%; Cl = 6.02%; N = 2.37%; O = 18.98%.

The indentity of the product was confirmed by elementary analysis, infra-red and NMR spectra, qualitative tests for detection of beclomethasone and by spectrophotometric comparison of beclomethasone, 4-N-acetyl-aminomethylcyclohexanecarboxylic acid and the reaction product.

EXAMPLE 2

Preparation of dexamethasone 21-(4-N-acetyl-aminomethylcyclohexanecarboxylate).

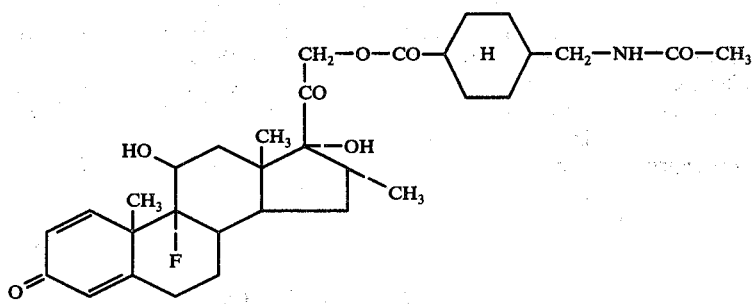

1 gram of dexamethasone was dissolved in 10 cm³ of anhydrous pyridine. This solution was poured into 10 cm³ of a solution obtained by dissolving 0.8 grams of the acid chloride (III) of Example 1 in anhydrous chloroform. The mixture was allowed to stand for 48 hours, then the solvent was evaporated off under vacuum. A solid product was obtained which was crystallized from ethanol.

Melting point 198° C; Molecular weight 573.47; Empirical formula $C_{32}H_{44}FNO_7$; C = 66.96%; H = 7.67%; F = 3.31%; N = 2.44%; O = 19.53%.

The identity of the product was confirmed by elementary analysis, infra-red and NMR spectra, qualitative tests for detection of dexamethasone and by spectrophotometric comparison of dexamethasone, 4-N-acetyl-aminomethylcyclohexanecarboxylic acid and the reaction product.

The new compounds, while conserving the typical activity of corticoidal substances, show more advantageous pharmacological and therapeutic properties. In particular, they have a more intense and prolonged activity, which may be achieved equally by topical, dermal application or using an aerosol.

Accordingly the invention also provides a therapeutic composition containing as active principle a compound of formula (I).

The active principle is generally in admixture with a therapeutically administrable vehicle or excipient.

For purposes of illustration, results of a toxicological and pharmacological study are given thereunder.

Toxicological Tests

In common with other derivatives of cortisone, the new products have no significant toxicity whether they are administered orally, parenterally, rectally or topically. They have the advantage, when compared with cortisone, that they have less effect on the calcium or protein metabolism. If the starting molecules are considered, it is seen that there are no modifications in the elimination of potassium, sodium or water.

Compared to the base steroid (dexamethasone and beclomethasone respectively), molecular weight being equal, the new product influences with less intensity (less than half) the experimental formation of gastric ulcers (by the method of Shay, by constriction and by glucose).

Pharmacological Test a. Test for corticoidal activity

What characterizes the new product in comparison to the base steroid, is a more prolonged corticoidal activity and a more powerful local action, whether dermal or bronchial.

The tests carried out (evaluation of the reduction of hematic corticosterone caused by inhibition of the hypophysis-suprarenal axis, an evaluation which can be considered parallel to the activity) confirm the prolonged action of the product.

Indeed, after having administered 2 mg/kg of dexamethasone, the level of plasmatic corticosterone returns to its initial values (30 mcg/100 cm³) after 15 hours, while after having administered equimolar quantities of dexamethasone 21-(4-N-acetyl-aminomethylcyclohexanecarboxylate), the corticoidal activity, after an identical period of time, was found to be still very high. (The levels are around 18 mcg/100 cm³ of plasma).

b. Anti-phlogistic activity

A comparison made between equimolar doses of dexamethasone and the new product showed, according to various tests made, a more intense anti-phlogistic action for the new product.

The tests carried out were on local oedemas of rat paws caused by carragheenin, dextran and serotonine. In the case of carragheenin-induced oedema, the administration of dexamethasone at a dose of 2 mg/kg caused a 50% reduction of the oedema, while administration of the equimolar dose with the new product prevented 70% of its formation.

The effect is even more evident by local application of the products on the paw with suitable excipients. In these last tests, while the effect of dexamethasone even at high concentrations (1%) does not appear significant, the application of its 21-(4-N-acetylaminomethyl-cyclohexanecarboxylate) at equimolar dose inhibits the appearance of the oedema of more than 50%.

The same more advantageous effects can be obtained by using beclomethasone 21-(4-N-acetyl-aminomethyl-cyclohexanecarboxylate) in comparison with beclomethasone.

c. Tests for anti-anaphylactic activity

By these tests it was possible to observe that bronchospasm and anaphylactic shock, induced by a heterogeneous serum in sensitized guinea pigs, were blocked longer by the new product than by dexamethasone and beclomethasone.

In fact, even at a distance of 8 hours from the administration of dexamethasone and beclomethasone 21-(4-N-acetyl-aminomethyl-cyclohexanecarboxylate), it was possible to demonstrate the inhibition of the appearance of the shock and the prevention of the treated animals from death, while at the same time equimolar doses of dexamethasone and beclomethasone proved to be almost devoid of protective action.

It was equally possible to demonstrate a more favorable activity by tests on cutaneous oedema caused in rats by intradermal injection of an immunoserum. In these tests the administration of 2.5 mg/kg of dexamethasone and beclomethasone was inactive to protect the animals from the appearance of the oedema, while equimolar doses of dexamethasone-and beclomethasone-21-(4-N-acetyl-aminomethylcyclohexanecarboxylate) reduced the oedema of more than 50%.

Effects as much evident were obtained with the same test by topical application of the products. Actually dexamethasone and beclomethasone derivatives reduced the formation of the oedema of more than 50% at doses which were inactive for dexamethasone and beclomethasone base.

The tests carried out indicated that the new compounds of the present invention can be used more advantageously than the base steroid in human therapeutic treatment for all conditions responsive to steroids.

The pharmaceutical composition can be administered orally, parenterally, rectally, topically or by aerosol, in the form of tablets, pills, syrups, ampoules, powders, ointments, creams or lotions, the active ingredients being in admixture with appropriate vehicles or excipients.

Several non-limitative examples of pharmacological formulations of the compounds of the present invention are given below:
- tablets containing 1 to 10 mg of active ingredient,
- injectable ampoules containing 5 to 30 mg of active ingredient,
- suppositories containing 2 to 20 mg of active ingredient,
- ointments, lotions, solutions for aerosols, containing 0.025 to 2% of active ingredient.

The dose administerable each 24 hours varies according to the therapeutic requirements.

Having now described my invention what I claim as new and desire to secure by Letters Patent is:

1. A compound of the formula:

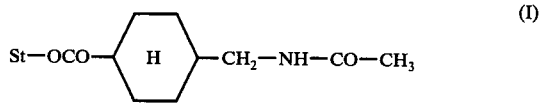

in which:

St represents a radical selected from 9-chloro-11β,17,21-trihydroxy-16β-methyl-pregna-1,4 diene-3,20-dione and 9-fluoro-11β,17,21-trihydroxy-16α-methyl-pregna-1,4 diene-3,20-dione, the ester linkage being at position 21 of the steroid group.

2. 9-chloro-11β,17,21-trihydroxy-16β-methyl-pregna-1,4 diene-3,20-dione 21-(4-N-acetylaminomethylcyclohexanecarboxylate).

3. 9-fluoro-11β,17,21-trihydroxy-16α-methyl-pregna-1,4 diene-3,20 dione 21-(4-N-acetylaminomethylcyclohexanecarboxylate).

4. A therapeutic composition having a corticoidal, anti-phlogistic and anti-anaphylactic activity comprising a compound of the formula:

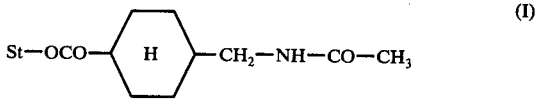

in which:

St represents a radical selected from 9-chloro-11β,17,21-trihydroxy-16β-methyl-pregna-1,4 diene-3,20 dione and 9-fluoro-11β,17,21-trihydroxy-16α-methyl-pregna-1,4 diene-3,20 dione, the ester linkage being at position 21 of the steroid group, in admixture with a therapeutically acceptable vehicle.

5. A composition according to claim 4, in unit dosage form.

* * * * *